United States Patent [19]

Cartwright

[11] 4,302,242
[45] Nov. 24, 1981

[54] HERBICIDAL MONO- OR DI-SUBSTITUTED-2-PYRIDINYLOXY-PHENOXY-LOWER-ALKANE-CARBAMATES

[75] Inventor: David Cartwright, Reading, England

[73] Assignee: Imperial Chemical Industries Limited, London, England

[21] Appl. No.: 165,125

[22] PCT Filed: Feb. 5, 1979

[86] PCT No.: PCT/GB79/00023

§ 371 Date: Oct. 15, 1979

§ 102(e) Date: Oct. 12, 1979

[87] PCT Pub. No.: WO79/00624

PCT Pub. Date: Sep. 6, 1979

[30] Foreign Application Priority Data

Feb. 15, 1978 [GB] United Kingdom ............... 6042/78

[51] Int. Cl.³ .................. C07D 213/64; A01N 43/40
[52] U.S. Cl. ........................................ 71/94; 546/291; 546/300; 546/302
[58] Field of Search ............... 546/291, 302, 300; 71/94

[56] References Cited

U.S. PATENT DOCUMENTS 4,046,553  9/1977  Takahashi et al. ............... 546/302
4,105,435  8/1978  Nishiyama et al. ............... 546/302

Primary Examiner—Alan L. Rotman
Attorney, Agent, or Firm—Cushman, Darby & Cushman

[57] ABSTRACT

Herbicidal pyridine compounds of the formula (I):

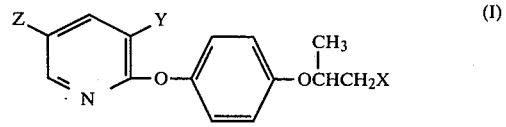

wherein Z may be halogen, or a fluorine- or chlorine-substituted alkyl group of 1 to 4 carbon atoms, and Y may be hydrogen, halogen, or a fluorine- or chlorine-substituted alkyl group of 1 to 4 carbon atoms; X may be an OH group or an acyloxy group; a halogen atom; an amino group, a mono- or di-alkyl amino group, or an alkanoylamido group; an alkoxy group optionally substituted by hydroxy or alkoxy; or a mercapto group, an alkylthio group, or a phenylthio group. The invention also provides herbicidal compositions containing the compounds, and processes for making the compounds.

4 Claims, No Drawings

HERBICIDAL MONO- OR DI-SUBSTITUTED-2-PYRIDINYLOXY-PHENOXY-LOWER-ALKANE-CARBAMATES

This invention relates to certain pyridine derivatives having herbicidal properties, and to herbicidal processes and compositions utilising them.

According to the present invention there are provided herbicidal pyridine compounds of the formula (I):

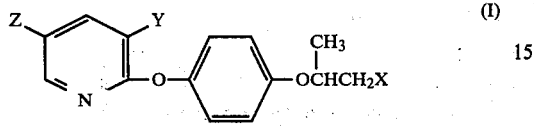

wherein Z represents fluorine, chlorine, bromine, iodine, or an alkyl radical of 1 to 4 carbon atoms substituted by one or more fluorine, or chlorine atoms, and Y represents hydrogen, fluorine, chlorine, bromine, iodine, or an alkyl radical of 1 to 4 carbon atoms substituted by one or more fluorine or chlorine atoms and X represents a hydroxy group; a fluorine, chlorine, bromine, or iodine atom; an $OCOR^1$ group in which $R^1$ is an alkyl group or a phenyl group optionally bearing one or more methyl groups or halogen atoms; an $-OCONR^2R^3$ group wherein $R^2$ represents hydrogen, an alkyl group of 1 to 4 carbon atoms, or a phenyl group, and $R^3$ represents an alkyl group of 1 to 4 carbon atoms or a phenyl group; an $-OSO_2NR^2R^3$ group; an $-OSO_2R^4$ group wherein $R^4$ is an alkyl group of 1 to 4 carbon atoms or a phenyl or tolyl group; an $-OSO_3R^4$ group; or an alkoxy group of 1 to 4 carbon atoms optionally substituted by one or more hydroxy groups or alkoxy groups of 1 to 4 carbon atoms; an SH or $SR^3$ group; or an amino group, an alkanoylamido group of 1 to 4 carbon atoms, or mono- or di-alkylamino group in which the one or two alkyl radicals each contain from 1 to 4 carbon atoms.

Examples of compounds according to the invention include those in which Z or Y is a trifluoromethyl group, and X is a hydroxy group. Particular examples of compounds according to the invention are listed in Table I.

TABLE I

| COMPOUND NO | Z | Y | X | Physical characteristic |
|---|---|---|---|---|
| 1 | $CF_3$ | Cl | OH | Oil |
| 2 | $CF_3$ | H | OH | Oil |
| 3 | $CF_3$ | H | Cl | $n_D^{25} = 1.5215$ |
| 4 | $CF_3$ | H | $OCOCH_3$ | $n_D^{24} = 1.5012$ |
| 5 | $CF_3$ | H | $OSO_2CH_3$ | $n_D^{24} = 1.5033$ |
| 6 | $CF_3$ | H | $OCONH\ CH_3$ | m.p. 82° C. |

When $R^1$ is an alkyl group it is preferably an alkyl group of 1 to 4 carbon atoms.

Further examples of compounds falling within the scope of the invention include the following:
2-[4-(5-difluoromethyl-2-pyridyloxy)phenoxy]-propanol
2-[4-(3-chloro-5-difluoromethyl-2-pyridyloxy)-phenoxy]-propanol
2-[4-(3,5-bis-trifluoromethyl-2-pyridyloxy)phenoxy]-propanol
2-[4-(5-chlorodifluoromethyl-2-pyridyloxy)phenoxy]-propanol
2-[4-(3-chloro-5-chlorodifluoromethyl-2-pyridyloxy)-phenoxy]propanol
2-[4-(3-bromo-5-trifluoromethyl-2-pyridyloxy)-phenoxy]-propanol
2-[4-(3-chloro-5-trifluoromethyl-2-pyridyloxy)-phenoxy]-propyl N-methylcarbamate
Methyl 2-[4-(5-trifluoromethyl-2-pyridyloxy)phenoxy]-propyl sulphate
Methyl 2-[4-(3-chloro-5-trifluoromethyl-2-pyridyloxy)-phenoxy]propyl sulphate
1-Acetamido-2-[4-(3-chloro-5-trifluoromethyl-2-pyridyloxy)phenoxy]propane
1-Acetamido-2-[4-(5-trifluoromethyl-2-pyridyloxy)-phenoxy]propane The compounds of the invention are herbicides which are in general substantially more effective against grass species than against broad-leaved species of plant. They may be used to control unwanted grass species growing alone, or at suitable rates of application they may be used to control grass weeds growing among broad-leaved crop plants. The compounds are more effective against unwanted plants when they are applied to the soil before the unwanted plants emerge than when they are applied directly to the above-ground parts of growing plants.

In another aspect, therefore, the invention provides a process of inhibiting the growth of unwanted plants, particularly grass species, which comprises applying to the locus of the plants, before the plants emerge, a herbicidally effective amount of a compound of formula (I) as hereinbefore defined.

The amount of the compound to be applied will depend upon a number of factors, for example the particular plant species whose growth is to be inhibited, but in general an amount of from 0.1 to 5 kilograms per hectare is usually suitable. The skilled worker in the art will readily be able to determine suitable amounts for use by means of standardised routine tests, without undue experimentation.

The compounds of the invention are preferably applied in the form of compositions, in which the active ingredient is mixed with a carrier comprising a solid or liquid diluent. Preferably the composition further comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, disper-sions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triiso-propyl-naphthalenesulphonic acid. Suitable agents of the non-ionic type include, for example, the condensation products of ethylene oxide with fatty alcohols such as oleyl alcohol and cetyl alcohol, or with alkyl phenols such as octyl-phenol, nonylphenol, and octylcresol. Other non-ionic agents are the partial esters derived from long chain fatty acids and hexitol anhydrides, for example sorbitol mono-laurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment. In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

The compounds of the invention may be prepared by the route outlined in Scheme A below:

Scheme A

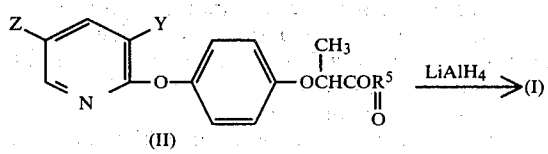

In Scheme A an ester (II) is reduced to the corresponding alcohol (I) by means of lithium aluminium hydride. Conveniently the reaction is carried out in a diluent, for example in a liquid hydrocarbon or ether. A particularly preferred solvent is tetrahydrofuran. The required alcohol derivative (I) may be isolated from the reaction mixture by conventional methods. Thus the reaction mixture may be diluted with tetrahydrofuran containing dissolved water to destroy any remaining lithium aluminium hydride, and then concentrated under reduced pressure. The alcohol (I) may then be isolated by extraction with a solvent.

In Scheme A above, the symbols X and Y have the meanings previously assigned to them, and $R^5$ is a alkyl radical, for example an alkyl radical of 1 to 4 carbon atoms. As well as lithium aluminium hydride, other hydride reducing agents may be used, for example sodium borohydride.

The esters (II) required as starting materials are themselves believed to be new compounds. They may be prepared as shown in Scheme B below:

Scheme B

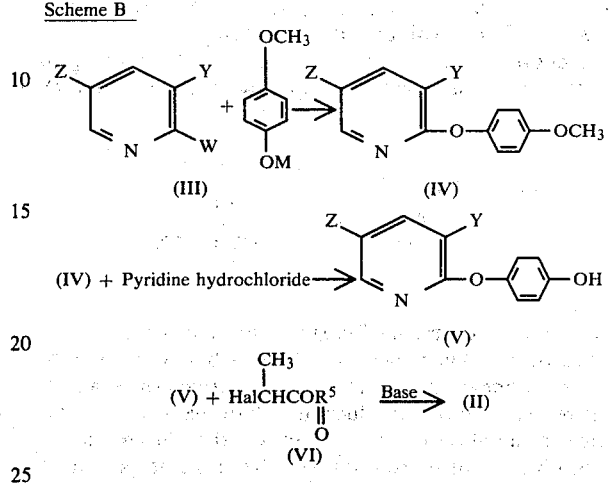

In Scheme B, the symbols Y, Z, and $R^5$ have the meanings previously assigned to them. The symbol W stands for a halogen atom, preferably fluorine, chlorine or bromine, and M is a cation, for example sodium. According to Scheme B, a suitably substituted halogeno-pyridine (III) is reacted with a metal salt of p-methoxyphenol, for example the sodium salt of p-methoxyphenol. The reaction is preferably carried out in a solvent, for example methyl ethyl ketone or tetrahydrofuran. The p-methoxyphenoxy compound (IV) so obtained is then demethylated by a standard procedure, for example by heating with pyridine hydrochloride, to obtain the corresponding p-hydroxy compound (V). This is in turn reacted in the form of its metal salt (for example the sodium or potassium salt) with the appropriate halogeno-alkanoic acid derivative (VI) to obtain the required compounds (II). Preferably this reaction is carried out in a solvent or diluent, for example methyl ethyl ketone.

A further method of preparing the esters (II) is shown in Scheme C below:

Scheme C

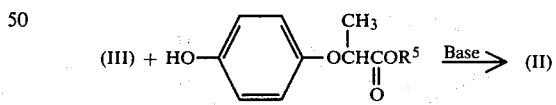

In Scheme C the symbols have the meanings previously assigned to them. In Scheme C a halogeno-pyridine (III) is reacted with a 2(4-hydroxyphenoxy)propionic ester in the presence of a base to give the ester (II). The base may be, for example an alkali metal carbonate, for example anhydrous sodium or potassium carbonate. The reaction is preferably carried out in a solvent or diluent. Suitable solvents include ketones, for example methyl ethyl ketone. The reaction may be accelerated by heating. At the end of the reaction period the product may be isolated by conventional methods, for example by filtering off insoluble salts from the reaction mixture and removing the solvent under reduced pressure to leave the product.

A further method of preparing the compounds of the invention wherein X is OH is shown in Scheme D below:

Scheme D

(V) + CH₃CHBrCH₂OH —Base→ (I, X = OH)

In Scheme D, the intermediate (V) prepared according to Scheme B is reacted with 2-bromopropanol in the presence of a base; the reaction conditions are similar to those described for the process of Scheme C.

A further method of preparing compounds of the invention in which X is OH is shown in Scheme E.

Scheme E

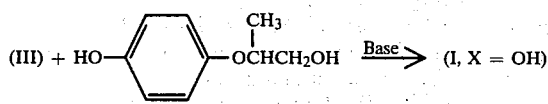

In Scheme E, a halogenopyridine (III) is reacted with 2 (4-hydroxyphenoxy) propanol in the presence of a base under the conditions described for the process of Scheme C. The 2(4-hydroxyphenoxy) propanol may itself be prepared by reacting hydroquinone with 2-bromopropanol in the presence of a base under the reaction conditions described for the process of Scheme C.

The halogenated pyridines (III) used in the processes of the above Schemes are believed to be new in themselves. They may be prepared by halogenation of appropriate 2-halogeno-5- or 3-methylpyridines. Thus, 2-chloro-5-trifluoromethyl-pyridine may be obtained by chlorinating 2-bromo-5-methyl-pyridine in the presence of ultra-violet light to obtain 2-chloro-5-trichloromethylpyridine. This may then be converted to 2-chloro-5-trifluoromethylpyridine by reaction with a fluorinating agent, for example antimony trifluoride or liquid hydrogen fluoride.

Compounds in which X is halogen may be prepared by treating compounds in which X is OH with a halogenating agent, for example thionyl chloride, phosphorus pentachloride, or phosphorus pentabromide. Compounds in which X is an acyloxy group may be prepared by acylating compounds in which X is an OH group by conventional procedures. Compounds in which X is —SH or —SR³ may be prepared from compounds in which X is halogen by reaction with a metal hydrosulphide or a metal salt of an appropriate mercaptan. Compounds in which X is amino, or mono- or dialkylamino may be prepared from compounds in which X is halogen by reaction with appropriately substituted amines. Acylamino compounds may be prepared by acylating compounds in which X is amino or alkylamino.

The invention is illustrated by the following Examples, in which all parts are by weight and all temperatures in degrees Centigrade unless otherwise specified.

EXAMPLE 1

This Example describes the preparation of 2[4(3-chloro-5-trifluoromethylpyridyl-2-oxy)phenoxy]propanol. (Compound no 1 of Table I).

Methyl α-[4(3-chloro-5-trifluoromethylpyridyl-2-oxy)phenoxy]propionate (1.9 g) in dry tetrahydrofuran (25 ml) was treated at room temperature with lithium aluminium hydride (0.20 g; an excess) in portions. Tetrahydrofuran containing dissolved water was added to the reaction mixture and the mixture evaporated under reduced pressure. The remaining oil was mixed with dilute sulphuric acid and the solution extracted with ether (80 ml). The ether extract was washed with water, dried, and evaporated to give a pale yellow oil, purified by passage through a column of silica gel, using chloroform containing 2% of ethanol as the eluent. The oil was identified as compound no 1 by its nuclear magnetic resonance spectrum and mass spectrum.

Following the same procedure, but using ethyl α-[4(5-trifluoromethylpyridyl-2-oxy)phenoxy]propionate as starting material, compound no 2 of Table I was obtained as an oil; the identity of the product was confirmed by its nuclear magnetic resonance spectrum.

EXAMPLE 2

This Example illustrates the preparation of the ethyl and methyl esters of α-4(3-chloro-5-trifluoromethyl-pyridyl-2-oxy)phenoxypropionic acid, the methyl ester being the starting material used in Example 1 to make compound no 1.

(a) Preparation of 2-amino-3-bromo-5-methylpyridine

2-Amino-5-methylpyridine (108 g) in glacial acetic acid (300 ml) was heated to 90°–100° C. while bromine (160 g) in acetic acid (55 ml) was slowly added with stirring. When addition was complete, the mixture was stirred and heated for a further 30 minutes and then allowed to cool overnight. The solid which separated was filtered off and mixed with ice and the mixture neutralised with concentrated ammonia, keeping the temperature at 0° to 5° C. The solid was collected, washed with water, and dried to give the bromo-compound.

(b) Preparation of 3-bromo-2-chloro-5-methylpyridine

The product from (a) (145 g) was dissolved in concentrated hydrochloric acid (750 ml) and water (450 ml) and the solution cooled to −10° C. Sodium nitrite (54 g) in cold water (450 ml) was added dropwise with stirring over a period of 90 minutes while the mixture was kept at −5° C. The solution was stirred for a further 2 hours, and then basified with concentrated ammonia, keeping the temperature below 20° C. The solid which separated was washed with water, dried, dissolved in ether (1500 ml) and washed with cold sodium hydroxide solution (1 M; 1 liter). The ether solution was washed twice with water (1 liter portions), dried, and evaporated to give the required 3-bromo-2-chloro-5-methyl-pyridine.

(c) Preparation of 2,3-dichloro-5-trichloromethylpyridine

The product from (b) (64 g) in dry carbon tetrachloride (650 ml) was treated with dry hydrogen chloride. The precipitate was broken up and the suspension heated under reflux while dry chlorine was bubbled into the mixture, with illumination from an ultra-violet light source. After 4½ hours, the mixture was cooled, filtered, and the filtrate evaporated to give the required 2,3-dichloro-5-trichloromethylpyridine. The mass spectrum was consistent with the structure assigned to this compound.

(d) Preparation of 2,3-dichloro-5-trifluoromethylpyridine

The product from (c) (1.0 g) and antimony trifluoride (3.0 g) were heated together at 170°–180° for 30 minutes. The mixture was then cooled, mixed with ice and water, and extracted with ether. The ether extracts gave a brown oil containing a mixture of 2,3-dichloro-5-trifluoromethylpyridine and 3-chloro-2-fluoro-5-trifluoromethylpyridine with a minor amount of 2,3-dichloro-5-chlorodifluoromethylpyridine.

(e) Preparation of 3-chloro-2-p-methoxyphenoxy-5-trifluoromethylpyridine p-Methoxyphenol (1.5 g) was added to a suspension of sodium hydride (0.6 g 50% oil dispersion, washed with petroleum) in dry dimethyl sulphoxide (30 ml) and the mixture stirred for 15 minutes. A solution of the combined products (1.5 g) from several preparations carried out as described in paragraph (d), in dimethylsulphoxide (20 ml) was added to the reaction mixture and heated to 60° C. for four hours. A further amount of sodium hydride (0.3 g of 50% oil dispersion, washed with petroleum), and potassium carbonate (1.38 g) was added. Heating was continued for another 4 hours. The mixture was poured into ice and water, and extracted with ether (400 ml). The ether extracts were washed with water, dilute sodium hydroxide, and water, dried, and evaporated to give the product.

(f) Preparation of 3-chloro-2-p-hydroxyphenoxy-5-trifluoro methylpyridine

The product from (e) (2 g) was heated with pyridine hydrochloride (20 g) at 170°–180° C. for 6 hours. The mixture was cooled, diluted with dilute hydrochloric acid, and extracted with ether. The ether extracts gave an oily solid which was purified by preparative thin layer chromatography using silica as the adsorbent and 6% ethanol-chloroform as the solvent.

(g) Preparation of ethyl alpha[4(3-chloro-5-trifluoromethylpyridyl-2-oxy)-phenoxy]propionate The product from (f) (0.16 g), ethyl alpha bromopropionate (0.3 g), and potassium carbonate (0.25 g) were heated and stirred under reflux in methyl ethyl ketone (10 ml) for 2 hours. The mixture was cooled and filtered. Evaporation of the filtrate gave an oil which was heated in a vacuum to remove traces of solvent. The oil was identified as the required ester by examination of its mass spectrum and its purity was confirmed by gas-liquid chromatography.

Following the same procedure, but using methyl alphabromopropionate instead of ethyl alphabromopropionate, methyl alpha[4(3-chloro-5-trifluoromethylpyridyl-2-oxy)phenoxy]propionate was prepared.

EXAMPLE 3

This Example illustrates the preparation of the starting material for the preparation of compound no 2 of Table I.

(a) Preparation of 2-chloro-5-trichloromethylpyridine

2-Bromo-5-methylpyridine (27 g) in dry carbon tetrachloride (500 ml) was treated with dry hydrogen chloride to give the hydrochloride salt. The solid which separated was broken up and the mixture heated to reflux. Chlorine was passed through the boiling mixture for 8 hours with irradiation by an ultra-violet lamp. The mixture was then filtered and evaporated to a pale yellow liquid which solidified on cooling. This was identified as the required chloro compound by its nuclear magnetic resonance spectrum.

(b) Preparation of 2-chloro-5-trifluoromethylpyridine and 2-chloro-5-difluorochloromethylpyridine The product from (a) (18 g) and antimony trifluoride (50 g) were heated together at 140°–145° C. for 1 hour. The mixture was cooled, mixed with ice and concentrated hydrochloric acid, and extracted with ether. The extracts were washed with water, dried with magnesium sulphate, and evaporated. The products from several such preparations were combined and distilled at atmospheric pressure through a short column packed with Fenske rings. The product boiling at 124°–154° C. was collected and identified as 2-chloro-5-trifluoromethylpyridine. Higher boiling fractions were redistilled at a pressure of 20 mm mercury to give 2-chloro-5-difluorochloromethylpyridine, boiling at 82° to 90° C.

(c) Preparation of 2-p-methoxyphenoxy-5-trifluoromethylpyridine

The product from (b) boiling at 124°–154° C. (1.82 g) was added in dry dimethylsulphoxide (15 ml) to a solution of p-methoxyphenol (1.24 g) in dimethylsulphoxide (20 ml) previously reacted with sodium hydride (0.48 g of a 50:50 oil dispersion). The mixture was stirred and heated to 60° to 65° for 5 hours, poured into ice, and extracted with ether. The ether extracts gave an oil.

(d) Preparation of 2-p-hydroxyphenoxy-5-trifluoromethylpyridine

The product from (c) (1.7 g) and excess of pyridine hydrochloride were heated together for 8 hours at 180° C. The mixture was cooled, diluted with water and 2-molar hydrochloric acid, and extracted with ether. The extracts were dried and evaporated to yield an oil identified as the required hydroxy compound.

(e) Preparation of ethyl alpha 4(5-trifluoromethylpyridyl-2-oxy)phenoxy propionate The product from (d) (0.22 g), ethyl alpha-bromopropionate (0.24 g) and potassium carbonate (0.18 g) in methyl ethyl ketone (5 ml) were stirred, and heated under reflux for 2 hours. The mixture was left to cool overnight, then filtered, and the residue washed with methyl ethyl ketone. The filtrate and washings were evaporated and the remaining oil subjected to a high vacuum to remove traces of solvent. The nuclear magnetic resonance spectrum of the oil was consistent with the structure assigned.

EXAMPLE 4

This Example illustrates the preparation of Compound No. 3 of Table I.

Compound No. 2 (1.0 g) was stirred at room temperature in thionyl chloride (10 ml) for 90 minutes and then heated under reflux for 6 hours. After 3 hours dimethylformamide (a few drops) was added to catalyse the reaction. The excess of thionyl chloride was removed under reduced pressure and the residue treated with ice and water and extracted with ether. The ether extract was washed with water, dried and evaporated to give a yellow oil. This was purified by chromatography on silica gel using chloroform containing 2% of ethanol as the solvent. The viscous oil so obtained (refractive index $n_D^{24} = 1.5215$) was identified by its NMR spectrum as 1-chloro-2-[4-(5-trifluoromethyl-2-pyridyloxy)-phenoxy]propane (0.9 g) (Compound No. 3 of Table I).

EXAMPLE 5

This Example illustrates the preparation of compound No. 4 of Table I.

Compound No. 2 (1 g) was stirred with acetic anhydride (10 ml) containing pyridine (a few drops) for 1 hour at room temperature. The excess of acetic anhydride was removed under reduced pressure. The residue was shaken with water and ether and the ether extract washed with water, dried, and evaporated to give an oil. This was purified by chromatography on silica gel using chloroform containing 2% ethanol as the solvent. The product, an oil ($n_D^{24} = 1.5012$) was identified as 1-acetoxy-2[4-(5-trifluoromethyl-2-pyridyloxy)-phenoxy]propane (1.07 g) by its NMR and IR spectrum.

EXAMPLE 6

This Example illustrates the preparation of Compound 5 of Table 1.

Compound No. 2 (1.0 g) and triethylamine (0.5 g) in methylene chloride (25 ml) were stirred with cooling at 10° C. while methanesulphonyl chloride (0.4 g) was added dropwise over a period of 5 minutes. The mixture was allowed to warm to room temperature and stirred for 1 hour, then left overnight. The solvent was removed under reduced pressure and the residue stirred with ether. The mixture was filtered and the filtrate evaporated to give a yellow oil. This was purified by chromatography on silica gel using chloroform containing 2% of ethanol as the solvent. The purified product, an oil (1.20 g) was identified as 1-methanesuphonyloxy-2-[4-(5-trifluoromethyl-2-pyridyloxy)phenoxy]propane by its NMR and IR spectrum; it had a refractive index ($n_D^{24}$) of 1.5033.

EXAMPLE 7

This Example illustrates the herbicidal properties of the compounds used in the process of the invention. Each compound was formulated for test by mixing it with 5 ml of an emulsion prepared by diluting 100 ml of a solution containing 21.8 grams per liter of Sapn 80 and 78.2 grams per liter of Tween 20 in methyl cyclohexanone to 500 ml with water. Span 80 is a Trade Mark for a surface-active agent comprising sorbitan monolaurate. Tween 20 is a Trade Mark for a surface-active agent comprising a condensate of twenty molar proportions of ethylene oxide with sorbitan mono-oleate. The mixture of the compound and the emulsion was shaken with glass beads and diluted to 12 ml with water.

The spray composition so prepared was sprayed on to young pot plants (post-emergence test) of the species named in Table II below, at a rate equivalent to 1000 liters per hectare. Damage to plants was assessed 14 days after spraying by comparison with untreated plants, on a scale of 0 to 3 where 0 is no effect and 3 represents 75 to 100% kill. In a test for pre-emergence herbicidal activity, seeds of the test species were placed on the surface of fibre trays of soil and were sprayed with the compositions at the rate of 1000 liters per hectare. The seeds were then covered with further soil. Three weeks after spraying, the seedlings in the sprayed fiber trays were compared with the seedlings in unsprayed control trays, the damage being assessed on the same scale of 0 to 3. The results are given in Table II below:

TABLE II

| COMPOUND NO | RATE OF APPLICATION kg/ha | PRE- OR POST-EMERGENCE APPLICATION | TEST PLANTS | | | | | |
|---|---|---|---|---|---|---|---|---|
| | | | Lt | To | Ot/Av | Ll | Cn | St |
| 1 | 0.02 | Pre | 0 | 0 | 2 | 3 | 0 | 3 |
| 1 | 0.02 | Post | 0 | 0 | 0 | 0 | 0 | — |
| 1 | 0.08 | Pre | 0 | 0 | 3 | 3 | 0 | 3 |
| 1 | 0.08 | Post | 0 | 0 | 1 | 0 | 0 | — |
| 2 | 0.02 | Pre | 0 | 0 | 0 | 3 | 0 | 0 |
| 2 | 0.02 | Post | 0 | 0 | 0 | 0 | 0 | — |
| 2 | 0.08 | Pre | 0 | 0 | 2 | 3 | 0 | 3 |
| 2 | 0.09 | Post | 0 | 0 | 0 | 0 | 0 | — |

The names of the test plants are as follows:

| Lt | Lettuce |
|---|---|
| To | Tomato |
| Ot/Av | Cultivated oats and wild oats (*Avena fatua*). Wild oats are used in the post-emergence test and cultivated oats in the pre-emergence test. |
| Ll | *Lolium perenne* (perennial rye grass) |
| Cn | *Cyperus rotundus* |
| St | *Seteria viridis* |

EXAMPLE 8

This Example illustrates the herbicidal properties of compounds of Table 1. The compounds were submitted to herbicide tests as described below.

Each compound was formulated for test by mixing an appropriate amount of it with 5 ml of an emulsion prepared by diluting 160 ml of a solution containing 21.8 grams per liter of Span 80 and 78.2 grams per liter of Tween 20 in methylcyclohexanone to 500 ml with water. Span 80 is a Trade Mark for a surface-active agent comprising sorbitan monolaurate. Tween 20 is a Trade Mark for a surface-active agent comprising a condensate of 20 molar proportions of ethylene oxide with sorbitan monolaurate. The mixture of the compound and the emulsion was then shaken with glass beads and diluted to 40 ml with water.

Seeds of the test species were placed on the surface of fibre trays of soil and were sprayed with the compositions so prepared at the rate of 1000 liters per hectare. The seeds were then covered with further soil. Three weeks after spraying, the seedlings in the sprayed fibre trays were compared with the seedlings in unsprayed control trays, the damage being assessed on a scale of 0 to 5, where 0 is 0 to 20% damage and 5 is complete kill.

The results of the tests are given in Table III below. Where a dash (-) appears, this means that no test was made.

TABLE III

| COMPOUND NO | RATE OF APPLICATION kg/ha | TEST PLANTS | | | | | | | | | | | | | |
|---|---|---|---|---|---|---|---|---|---|---|---|---|---|---|---|
| | | Sb | Rp | Ct | Sy | Mz | Ww | Rc | Or | Dg | Pu | St | Ec | Sh | Ag |
| 1 | 0.005 | 2 | 0 | 0 | 1 | 0 | 0 | 0 | 0 | 2 | 0 | 1 | 0 | 0 | 1 |

TABLE III-continued

| COMPOUND NO | RATE OF APPLICATION kg/ha | TEST PLANTS |||||||||||||| 
|---|---|---|---|---|---|---|---|---|---|---|---|---|---|---|
| | | Sb | Rp | Ct | Sy | Mz | Ww | Rc | Or | Dg | Pu | St | Ec | Sh | Ag |
| | 0.01 | 1 | 0 | 0 | 1 | 0 | 0 | 2 | 0 | 4 | 0 | 3 | 1 | 0 | 0 |
| | 0.02 | 2 | 1 | 2 | 0 | 1 | 0 | 2 | 1 | 4 | 2 | 3 | 2 | 0 | 1 |
| | 0.04 | 2 | 0 | 2 | 0 | 2 | 3 | 2 | 3 | 4 | 4 | 4 | 3 | 2 | 2 |
| 2 | 0.01 | 0 | 0 | 2 | 0 | 0 | 0 | 0 | 0 | 2 | 0 | 0 | 0 | — | 0 |
| | 0.02 | 0 | 0 | — | 0 | 1 | 0 | 2 | 1 | 3 | 1 | 2 | 0 | 2 | — |
| | 0.04 | 0 | 0 | 1 | 0 | 2 | 0 | 2 | 0 | 4 | 1 | 2 | 0 | 2 | 0 |
| | 0.08 | 2 | 0 | 2 | 0 | 2 | 3 | 3 | 0 | 4 | 1 | 4 | 5 | 4 | 3 |

Names of test plants in Table III

| | |
|---|---|
| Sb | Sugar beet |
| Rp | Rape |
| Ct | Cotton |
| Sy | Soya bean |
| Mz | Maize |
| Ww | Winter wheat |
| Rc | Rice |
| Ot | Oats |
| Dg | *Digitaria sanguinalis* |
| Pu | *Poa annua* |
| St | *Setaria viridis* |
| Ec | *Echinochloa crus-galli* |
| Sh | *Sorghum halepense* |
| Ag | *Agropyron repens* |

The compounds of the invention may be used in admixture with other herbicides. Accordingly the invention further provides a herbicidal composition comprising a mixture of at least one herbicide of formula (I) above with at least one other herbicide.

The other herbicide may be any herbicide not having the formula (I). It may be a herbicide having a similar spectrum of herbicidal effect, that is to say a herbicide mainly effective against grasses, or it may be a herbicide having a complementary action, for example a herbicide that is active against broad-leaved weeds.

Examples of herbicides which may be mixed with the compounds of the invention include the following:
A. Bipyridylium herbicides, for example paraquat dichloride (1,1'-dimethyl-4,4'-bipyridylium dichloride) and diquat dibromide (1,1'-ethylene-2,2'-bipyridylium dibromide).
B. Glyphosate (N-phosphonomethylglycine) and its salts and esters.
C. Bentazon (3-isopropyl-(1H)-benzo-2,1,3-thiazine-4-one 2,2-dioxide).
D. Hormone herbicides
   e.g. MCPA (4-chloro-2-methylphenoxyacetic acid)
   2,4-D (2,4-dichlorophenoxyacetic acid)
   Dichlorprop (2-[2,4-dichlorophenoxy]propionic acid)
   2,4,5-T (2,4,5-trichlorophenoxyacetic acid) Mecoprop (2-[4-chloro-2-methylphenoxy]propionic acid).
E. Urea herbicides
   e.g. Chloroxuron (3-[4-(4-chlorophenoxy)phenyl]-1,1-dimethyl urea)
   Diuron (1-[3,4-dichlorophenyl]-3,3-dimethyl urea)
   Fluometuron (1-[metatrifluoromethylphenyl]-3,3-dimethyl urea).
F. Triazine herbicides
   e.g. simazine (2-chloro-4,6-diethylamino-1,3,5-triazine)
   atrazine (2-chloro-4-ethylamino-6-isopropylamino-1,3,5-triazine)
G. 1-alkoxy-1-alkyl-3-phenylurea herbicides
   e.g. linuron (3[3,4-dichlorophenyl]-1-methoxy-1-methyl urea)
   monolinuron (3-[4-chlorophenyl]-1-methoxy-1-methyl urea).
H. 1,2,4-Triazine-5-one herbicides
   e.g. metamitron (4-amino-4,5-dihydro-3-methyl-6-phenyl-1,2,4-triazin-5-one)
   metribuzin (4-amino-6-tertbutyl-4,5-dihydro-3-methylthio-1,2,4-triazin-5-one).
I. Anilide herbicides
   e.g. butachlor (N-butoxymethyl-α-chloro-2',6'-diethylacetanilide)
   alachlor (N-methoxymethyl-α-chloro-2',6'-diethylacetanilide)
   and propanil (3,4-dichloropropionanilide).
J. Haloalkanoic acids
   e.g. dalapon (2,2-dichloropropionic acid)
   TCA (trichloroacetic acid)
K. Diphenyl ether herbicides
   e.g. fluorodifen (4-nitrophenyl 2'-nitro-4'-trifluoromethylphenyl ether)
   2-nitro-5-(2-chloro-4-trifluoromethylphenoxy)benzoic acid
   and 2-chlorophenyl-3'-ethoxy-4'-nitro-4-trifluoromethylphenyl ether The mixtures of the invention generally contain from 0.1 to 10 parts, conveniently from 0.2 to 2 parts by weight of herbicide of formula (I) per part by weight of the other herbicide, depending upon the relative activity of the components. The amount of the mixture to be applied will depend upon a number of factors, for example the particular plant species to which the mixture is to be applied, but in general an amount of from 0.1 to 5.0 kilograms per hectare will usually be suitable.

I claim:
1. A herbicidal pyridine compound of the formula (I):

$$Z\text{-pyridyl}(Y)\text{-O-}C_6H_4\text{-OCH}(CH_3)CH_2X \quad (I)$$

wherein Z is trifluoromethyl and Y is hydrogen or chlorine; and X is $-OCONR^2R^3$ wherein $R^2$ is hydrogen, $C_{1-4}$ alkyl or phenyl and $R^3$ is $C_{1-4}$ alkyl or phenyl.

2. A process of inhibiting the growth of unwanted plants, which comprises applying to the locus of the plants, before their emergence, a compound as claimed in claim 1, in a herbicidally effective amount.

3. A process as claimed in claim 2, wherein the compound is applied at the rate of from 0.1 to 5 kilograms per hectare.

4. A herbicidal composition consisting essentially of as an active ingredient a compound as claimed in claim 1, in admixture with a carrier comprising a solid or liquid diluent.

* * * * *